United States Patent [19]
Klemm

[11] Patent Number: 5,458,605
[45] Date of Patent: Oct. 17, 1995

[54] COILED REINFORCED RETRACTABLE SLEEVE FOR STENT DELIVERY CATHETER

[75] Inventor: Kurt Klemm, Mountainview, Calif.

[73] Assignee: Advanced Cardiovascular Systems, Inc., Santa Clara, Calif.

[21] Appl. No.: 222,656

[22] Filed: Apr. 4, 1994

[51] Int. Cl.⁶ .......................... A61B 19/00; A61M 25/10
[52] U.S. Cl. .......................... 606/108; 606/194; 604/104; 604/282
[58] Field of Search ...................... 128/657, 772; 604/96, 104, 171, 264, 280, 282; 606/1, 108, 190–194, 198

[56] References Cited

U.S. PATENT DOCUMENTS

| | | |
|---|---|---|
| 4,516,972 | 5/1985 | Samson . |
| 4,538,622 | 9/1985 | Samson et al. . |
| 4,619,274 | 10/1986 | Morrison . |
| 4,652,259 | 3/1987 | O'Neil ........................... 604/171 |
| 4,665,918 | 5/1987 | Garza et al. ................... 606/108 |
| 4,748,982 | 6/1988 | Horzewski et al. ............. 604/160 |
| 4,775,371 | 10/1988 | Mueller, Jr. . |
| 4,893,623 | 1/1990 | Rosenbluth ..................... 604/104 |
| 4,947,864 | 8/1990 | Shockey et al. ................ 604/280 |
| 4,981,478 | 1/1991 | Evard et al. . |
| 5,021,059 | 6/1991 | Kensey et al. ................... 604/15 |
| 5,089,005 | 2/1992 | Harada .......................... 604/104 |
| 5,135,503 | 8/1992 | Abrams . |
| 5,176,661 | 1/1993 | Evard et al. . |
| 5,234,416 | 8/1993 | Macaulay et al. . |
| 5,263,963 | 11/1993 | Garrison et al. ............... 604/104 |
| 5,290,230 | 3/1994 | Ainsworth et al. . |
| 5,290,295 | 3/1994 | Querals et al. ................. 604/264 |
| 5,300,025 | 4/1994 | Wantink . |
| 5,300,032 | 4/1994 | Hibbs et al. ................... 604/265 |

FOREIGN PATENT DOCUMENTS 0473045 3/1992 European Pat. Off. .............. 604/282

Primary Examiner—Stephen C. Pellegrino
Assistant Examiner—Glenn K. Dawson
Attorney, Agent, or Firm—Fulwider Patton Lee & Utecht

[57] ABSTRACT

A coiled reinforced retractable sleeve that provides a stent delivery system with improved longitudinal stiffness, lateral flexibility and overall pushability while maintaining dimensional stability. The coil reinforced retractable sleeve includes a spiral wound ribbon encapsulated between an inner and an outer laminate which form an elongated tubular body adapted to slidably receive an intravascular catheter. The tubular body has a first end adapted to connect with a manipulating device for effecting relative longitudinal movement of the intravascular catheter and sleeve and having a second end adapted for egress and ingress of the intravascular catheter.

1 Claim, 3 Drawing Sheets

COILED REINFORCED RETRACTABLE SLEEVE FOR STENT DELIVERY CATHETER

BACKGROUND OF THE INVENTION

This invention relates to devices for treatment of heart diseases and more particularly, to a retractable sleeve for use in a stent delivery system.

Several interventional treatment modalities are presently used for heart disease including balloon and laser angioplasty, atherectomy and by-pass surgery. In typical balloon angioplasty procedures, a guiding catheter having a preformed distal tip is percutaneously introduced through the femoral artery into the cardiovascular system of a patient in a conventional Seldinger technique and advanced within the cardiovascular system until the distal tip of the guiding catheter is seated in the ostium of a desired coronary artery. A guidewire is positioned within an inner lumen of a dilatation catheter and then both are advanced through the guiding catheter to the distal end thereof. The guidewire is first advanced out the distal end of the guiding catheter into the coronary vasculature until the distal end of the guidewire crosses a lesion to be dilated, then the dilatation catheter having an inflatable balloon on the distal portion thereof is advanced into the patient's coronary anatomy over the previously introduced guidewire until the balloon the dilatation catheter are properly positioned across the lesion.

Once in position across the lesion, the balloon, which is made of relatively inelastic materials, is inflated to predetermined size with radiopaque liquid at a relatively high pressure (e.g., greater than four atmospheres) to compress the arteriosclerotic plaque of the lesion against the inside of the arterial wall and to otherwise expand the inner lumen of the artery. The balloon is then deflated so that the blood flow can be resumed through the dilatated artery and the dilatation catheter can be removed therefrom. Further details of dilatation catheters, guidewires, and devices associated therewith for angioplasty procedures can be found in Simpson, et al. U.S. Pat. No. 4,323,071; Sampson, et al. U.S. Pat. No. 4,554,929; Simpson U.S. Pat. No. 4,616,652; Powell U.S. Pat. No. 4,638,805; and Horzewski, et al. U.S. Pat. No. 4,748,982, which are incorporated herein in their entirety by reference thereto.

A major focus of recent development work in the treatment of heart disease has been directed to endoprosthetic devices called stents. Stents are generally cylindrically-shaped intravascular devices which are placed within a damaged artery to hold it open. The device can be used to prevent restenosis and to maintain the patency of a blood vessel immediately after intravascular treatments. In some circumstances, they can also be used as the primary treatment device where they are expanded to dilate a stenosis and then left in place.

The rapid and effective delivery of a stent to a designated location within the patient's vasculature is desirable, particularly where the stent is to be delivered within a coronary artery. That is, quickly placing a stent within a patient's vasculature is desirable since the intrusive nature of the angioplasty procedure and the associated danger to the patient may then be minimized. It has been found to be difficult to quickly deliver a stent, however, particularly in those situations in which an intimal flap has occluded an artery.

Attempts to advance and place a stent in regions of coronary arteries occluded by dissected arterial linings have had varying degrees of success. A successful method for rapidly and effectively delivering a stent involves placing a compressed or otherwise small diameter stent about an expandable member, such as a balloon, on the distal end of an intravascular catheter and slidably disposing the intravascular catheter within an elongated sheath having a distal port through which the catheter may egress. Thereafter, the sheath and catheter may be advanced through the patient's vascular system until they are in the desired location within a blood vessel and the relative axial positions of the sheath and catheter may be manipulated so that the entire length of the stent mounted on the distal extremity of the catheter is emitted from the sheath. Next, the balloon catheter may be expanded so as to seat the stent within the blood vessel. Finally, the balloon catheter is deflated and the sheath and catheter are withdrawn, leaving the expanded stent within the blood vessel holding open the passageway thereof.

However, during the advancement through arduous turns of a patient's vasculature, the sheath and catheter of stent delivery systems heretofore provided may kink and buckle. The elongated portions of conventional systems may comprise homogeneous material selected to optimize longitudinal stiffness and lateral flexibility. In the selection of materials, however, it is necessary to compromise on stiffness or flexibility since homogeneous materials generally do not possess both and therefore, result in comprising structure that kinks and buckles. Kinking or buckling of stent delivery system structure may impede advancement thereof through a patient's vasculature or otherwise result in a damaged stent delivery system, necessitating removing the damaged system and repeating the procedure with a replacement system. Further, the patient's vasculature may be traumatized when a stent delivery catheter kinks and cannot be advanced in a tight turn. Since it is advantageous to quickly deliver a stent to a repair site within a patient's vasculature, a stent delivery system having improved stiffness, pushability and flexibility is desirable.

Accordingly, what is needed and heretofore unavailable is a stent delivery system comprising structure that avoids kinking and buckling while being advanced through a patient's vasculature. The present invention satisfies this need.

SUMMARY OF THE INVENTION

The invention provides a coil reinforced retractable sleeve, for use in a stent delivery system, that resists kinking and buckling and provides the stent delivery system with improved longitudinal stiffness, improved lateral flexibility and greatly enhanced pushability and retraction response while maintaining dimensional stability. By comprising greatly enhanced pushability and retraction response, a one to one ratio between the advancement into a patient's vasculature of a stent delivery system with respect to its advancement within the vasculature is approximated.

In a preferred embodiment, a coil reinforced retractable sleeve may embody an elongated tubular body comprising a spiral wound ribbon encapsulated between two laminates and may be produced using a manufacturing process that assures dimensional stability. It is contemplated that the laminated coil reinforced structure comprise a substantial portion of the retractable sleeve and extend distally from a manipulating device for causing axial motion of the retractable sleeve to a point proximal a distal end of the sleeve. The remaining or distal portion of the coil reinforced retractable sleeve is contemplated to comprise another material.

It is also contemplated that the spiral wound ribbon comprise relatively inelastic material so that each adjacent turn of the spiral translates an applied longitudinal force into advancing progression without a resulting elastic deformation in the ribbon material, thereby resulting in structure having improved stiffness. The spiral wound ribbon may comprise a relatively large number of turns, so that kinking and buckling may be resisted without substantially impeding lateral flexibility, thereby resulting in a structure having improved flexibility. Moreover, by selecting a laminate, such as polyimide, comprising material that resists buckling and kinking, the sleeve necessarily embodies superior flexibility. By comprising improved longitudinal stiffness and lateral flexibility, the sleeve necessarily possesses improved pushability and retraction response.

In addition, in a preferred embodiment the tubular coil reinforced retractable sleeve may be adapted to slidably receive an intravascular catheter, such as a balloon catheter, for delivering a stent to a designated area within a blood vessel and may further comprise a distal port through which the intravascular catheter may egress. Moreover, the sleeve may be adapted to connect to a manipulating device for retracting the sleeve or for effecting relative longitudinal movement of the sleeve and intravascular catheter.

In another embodiment, the laminated coiled reinforced structure may comprise the entire length of the retractable sleeve and may further comprise a distal end that tapers down in a substantially sphere-like manner so that the cross-sectional area is somewhat less in the distal region than the cross-sectional area of the rest of the sleeve. A coiled reinforced retractable sleeve having a tapered distal end comprises a profile well suited for traveling through a patient's vasculature. The sleeve may also incorporate a notch at its distal end for providing a softer and more flexible structure where desired. Further, the sleeve may embody a proximal port that is disposed in a wall of the retractable sleeve proximate to the distal port and that is adapted to receive a guidewire. It is also contemplated that the sleeve comprise a slot extending from the proximal port to a location just proximate to the distal port and functioning to facilitate relative movement of a guidewire through the retractable sleeve. Finally, the retractable sleeve may embody a plurality of slits formed in its wall which extend proximally from the distal port and which operate to enable the distal end to be compressed to a smaller cross-sectional profile.

In yet another embodiment, it is contemplated that the coil reinforced retractable sleeve further comprise a thin-walled material that encapsulates the inner and outer laminates. The thin-walled material functions to add strength to the sleeve as well as functions to resist kinking and its effects.

Other aspects and advantages of the invention will become apparent from the following detailed description, taken in conjunction with the accompanying drawings, which illustrate, by way of example the principles of the invention.

DETAILED DESCRIPTION OF THE PREFERRED EMBODIMENTS

Figure 1:
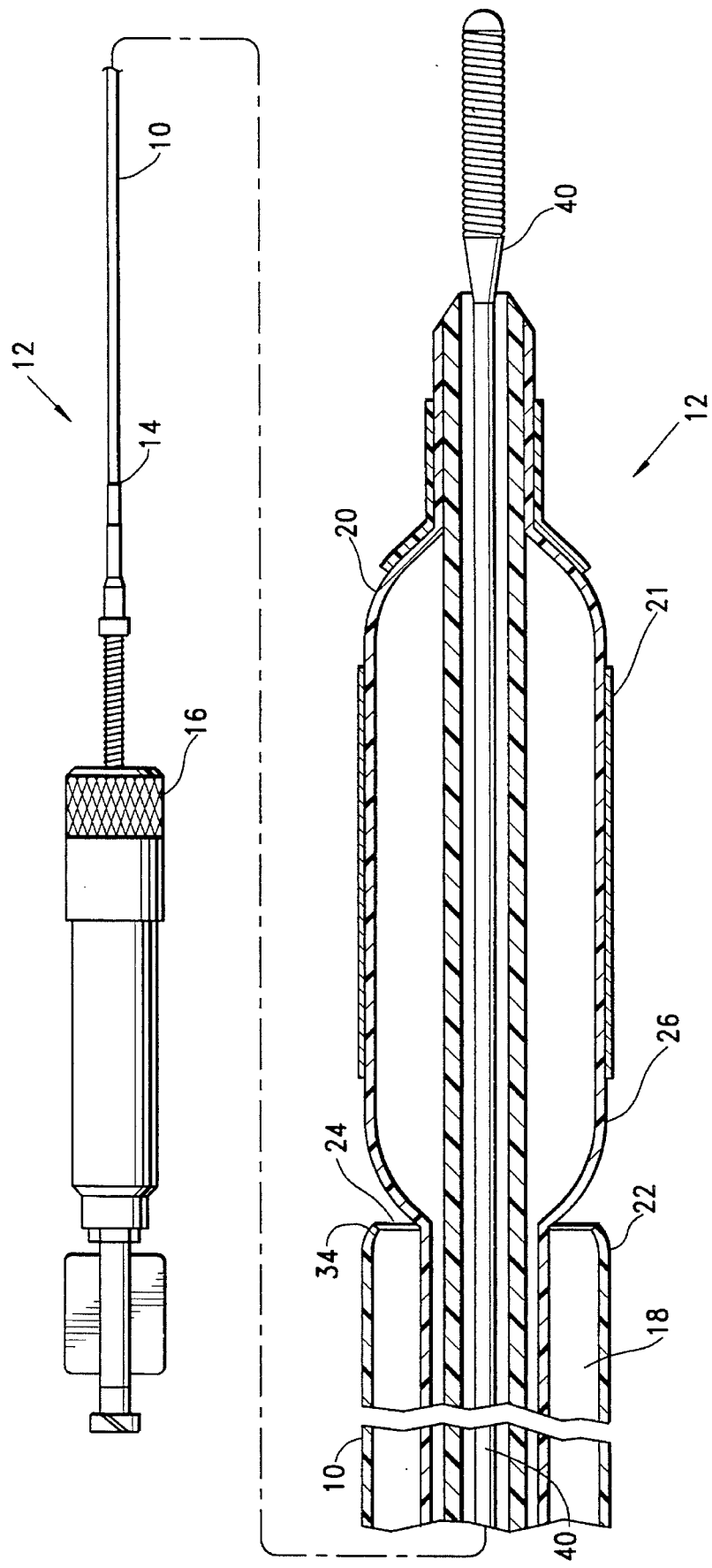
FIG. 1 is a partial longitudinal cross-sectional view of a stent delivery system which embodies the invention, illustrating a preferred embodiment of a coil reinforced retractable sleeve.

As is shown in the drawings, which are provided for purposes of illustration and not by way of limitation, the invention is embodied in a coil reinforced retractable sleeve that resists kinking and buckling and provides improved stiffness, flexibility, retractability and pushability while maintaining overall dimensional stability. Stent delivery systems found in the art accomplish placement of stents within a blood vessel but typically comprise structure that buckles and kinks during advancement through a patient's vasculature. Since the vasculature of a patient has many turns, a system that may advance through the vasculature while avoiding buckling and kinking is desirable. Further, since it is important to minimize the intrusive nature of delivering a stent within a patient's vasculature, it is advantageous to have a stent delivery system comprising structure with improved stiffness, flexibility and pushability so that a stent may be quickly placed within a blood vessel. Therefore, the coil reinforced retractable sleeve of the present invention is an improvement over conventional sleeves employed by stent delivery systems.

Figure 1A:
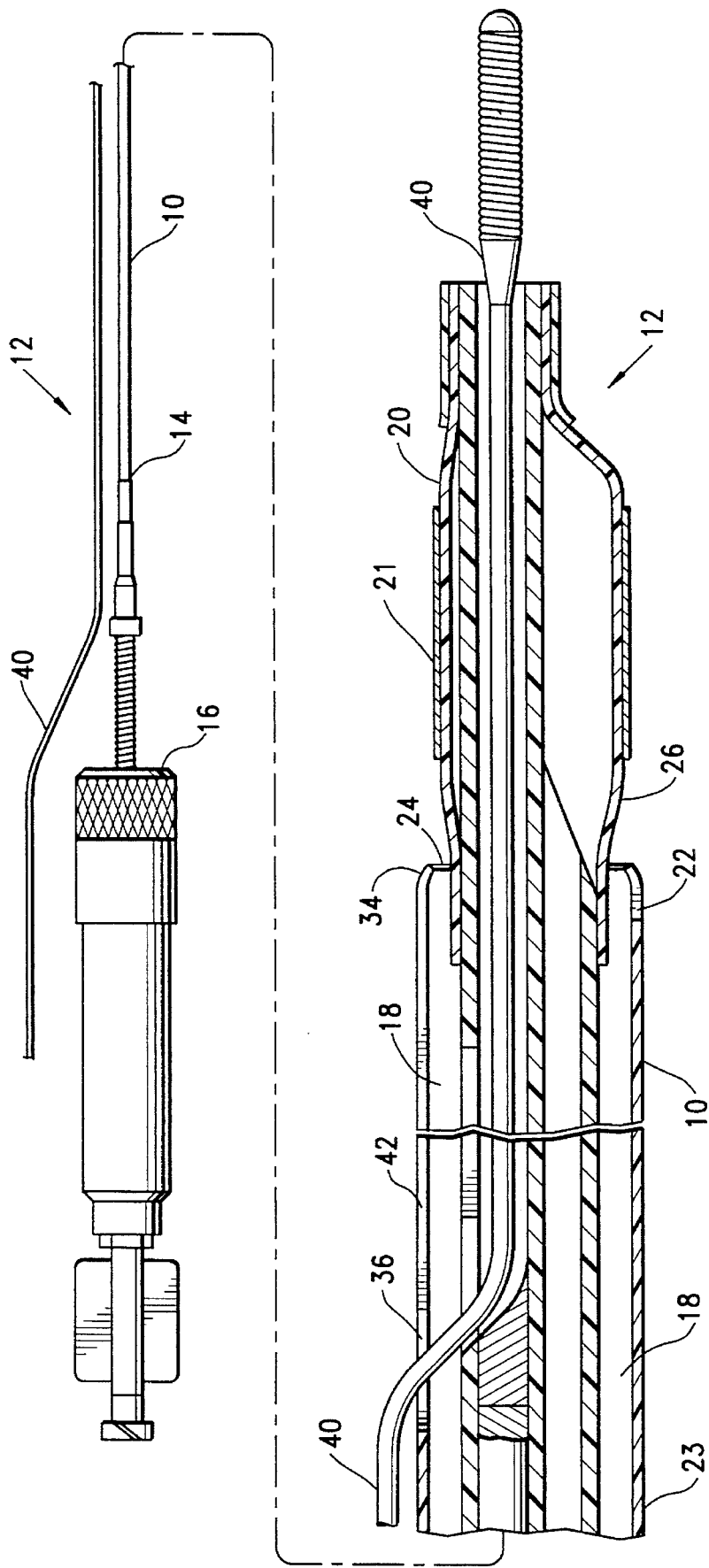
FIG. 1a is a partial longitudinal cross-sectional view of a stent delivery system which embodies the invention, illustrating one embodiment of a coil reinforced retractable sleeve.
Figure 2:
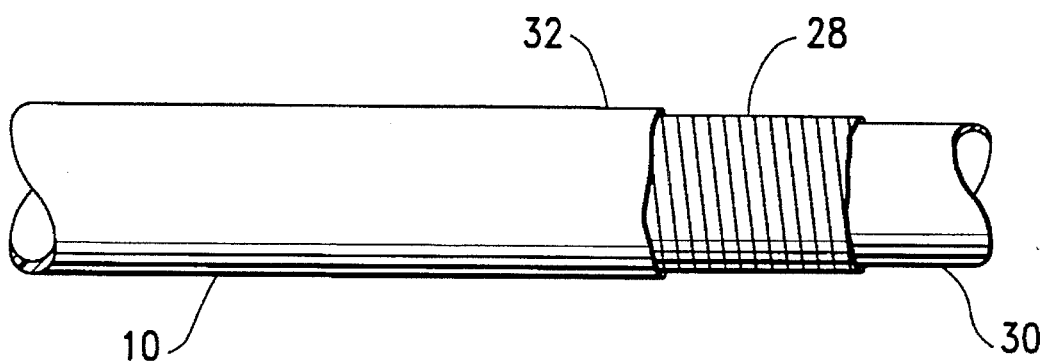
FIG. 2 is a partial segmented view of a preferred embodiment of the invention, illustrating a portion of a coil reinforced retractable sleeve having a wound ribbon interior encapsulated between an inner and an outer laminate.

Referring to FIGS. 1 and 1a, the present invention is embodied in a coiled reinforced retractable sleeve 10 for use in a stent delivery system 12. In a preferred embodiment, it is contemplated that the sleeve 10 comprise a spiral wound ribbon 28 encapsulated between an inner laminate 30 and an outer laminate 32 (See FIG. 2). It is also contemplated that the sleeve 10 comprise an elongated tubular body having a proximal end 14 adapted to connect to a manipulating device 16 for retracting the sleeve 10. Further, the sleeve may embody a hollow interior 18 adapted to slidably receive an intravascular catheter 20, such as a balloon catheter, for delivering a stent 21.

Figure 3:
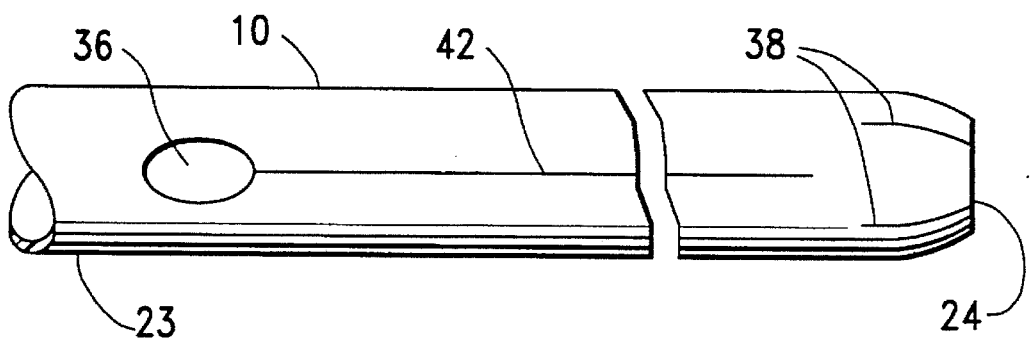
FIG. 3 is a top view of another embodiment of the invention, illustrating a coil reinforced sleeve comprising structure for expediting stent delivery.

The laminated coil reinforced structure may or may not extend the length of sleeve 10. In the preferred embodiment, the laminated coil reinforced structure extends to a point near a distal end 22 of the retractable sleeve. For example, the laminated coil reinforced portion may extend to a point 23 just proximal to port 36 (See FIGS. 1a and 3). The remaining length of sleeve 10 may comprise polyethylene or an equivalent composition that may be attached to the laminated coil reinforced portion 10 and may further comprise a distal end 22 having a distal port 24 formed therein. The distal port 24 may be of sufficient size to allow for, upon operation of the manipulating device 16, ingress and egress of an inflatable portion 26 of a balloon catheter retaining a stent 21.

In the preferred embodiment, the spiral wrapped ribbon 28 and inner 30 and outer 32 laminates comprise a sleeve 10 having a generally uniform cross-sectional area and constant diameter. The spiral wrapped ribbon 28 may comprise any relatively inelastic material, for example any metal, that may be produced having the geometric configuration of a ribbon and that may be spiral wrapped so as to take on a cylindrical form. It may be desirable to select the ribbon material with radiopaque characteristics in mind. In addition, it is contemplated that the spiral wound ribbon 28 comprise a relatively large number of turns per inch. For example, the spiral wound ribbon 28 may have between fifty and seventy windings per inch. It is to be understood that the more windings per inch of ribbon 28 the more flexible sleeve 10 becomes. By combining a relatively inelastic material and large number of turns per inch, ribbon 28 provides the sleeve 10 with improved longitudinal stiffness.

The laminates 30,32 may also comprise virtually any material that may be formed to encapsulate a spiral wound ribbon. In a preferred embodiment, it is contemplated that the laminates 30,32 be made from polyimide. Polyimide is an appropriate material since it resists kinking and buckling as well as possesses processing and mechanical characteristics suited for forming and encapsulating a tubular structure.

In order to construct a sleeve 10 having dimensional stability, the sleeve 10 may be manufactured by first producing the ribbon 28 and then molding the laminates 30,32 about the ribbon 28. In the alternative, it may be desirable to incorporate the winding of a ribbon 28 into a process for extruding tubing. Thereafter, the sleeve 10 may be cut to a length useful for delivering a stent 21 within a desired location of a blood vessel.

In another embodiment, the laminated coil reinforced portion extends the length of the sleeve 10 and may further comprise structure functioning to expedite the delivery of a stent within a patient's vasculature. The sleeve 10 includes a tapered distal end 34 that narrows in a sphere-like manner and a proximal port 36 disposed in a wall proximate to the distal end 22 of the sleeve (See FIGS. 1a and 3). A plurality of slits 38 extending proximally from the distal end of 22 and substantially parallel to a longitudinal axis of the sleeve 10. The slits 38 function to provide the stent delivery system 12 with a low profile well suited for traveling through a blood vessel. One or more notches 39 may also be incorporated into the distal end 22 in order to facilitate advancement the stent delivery system 12 through a blood vessel (See FIG. 4). Slot 42 extends distally from the proximal port 36 and substantially parallel to the longitudinal axis of the sleeve 10. The proximal port 36 provides a through hole for a guidewire 40 about which an intravascular catheter 20 and sleeve 10 travel and are guided to a desired location within a patient's vasculature. The slot 42 extending from the proximal port 36 facilitates the relative motion of the sleeve 10 and the guidewire 40.

Figure 4:
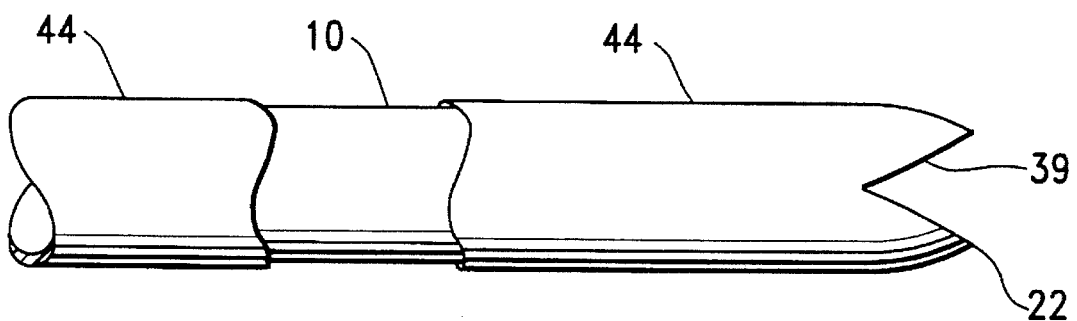
FIG. 4 is a partial cross-sectional view of yet another embodiment of the invention, illustrating a coil reinforced sleeve incorporating a notch for expediting stent delivery.

In yet another embodiment, the sleeve 10 may be further encapsulated with a thin-walled material (See for example FIG. 4). By further encapsulating the sleeve 10 with a thin-walled material, for example shrink tubing, the sleeve 10 may possess additional material strength while substantially retaining its improved pushability and kink resistance capability.

It is also contemplated that the coil reinforced structure of the sleeve 10 may be applied to all catheter shafts, inner members and outer members. In addition, it is contemplated that all catheter shafts, inner members and outer members as well as the sleeve solely comprise a polyimide material substantially having the pushability of a sleeve embodying a ribbon.

From the foregoing it will be appreciated that the invention provides a coil reinforced retractable sleeve 10 that resists kinking and buckling and that provides a stent delivery system with improved stiffness, flexibility, pushability and retraction response. As a stent delivery system incorporating the invention is advanced through a patient's vasculature, the coil reinforced retractable sleeve 10 resists kinking and buckling, thereby facilitating expedious delivery of a stent within a blood vessel.

While several particular forms of the invention have been illustrated and described, it will also be apparent that various modifications can be made without departing from the spirit and scope of the invention. Thus, it should be understood that various changes in form, detail and application of the present invention may be made without departing from the spirit and scope of this invention.

I claim:

1. A stent delivery system, comprising:

an elongate tubular body, said elongate tubular body having a proximal portion and a distal portion;

said proximal portion defined by an inner laminate and an outer laminate;

a spiral wound ribbon encapsulated between said inner laminate and said outer laminate;

an intravascular catheter slidably disposed within said tubular body, said catheter having an intravascular stent mounted thereon;

a manipulating device attached to a proximal end of said tubular body for effecting relative axial movement of said catheter with respect to said tubular body;

a passageway formed in a distal end of said tubular body to allow a portion of said catheter carrying said stent to pass therethrough;

a port formed in said tubular body, said port adapted for receiving a guidewire therethrough; and a slot formed in said tubular body, said slot extending from said port to a point proximate said passageway, said slot adapted for facilitating the relative movement of the guidewire and the tubular body.

\* \* \* \* \*